United States Patent [19]

Hargreaves et al.

[11] Patent Number: 4,558,045
[45] Date of Patent: Dec. 10, 1985

[54] 1,3,4-THIADIAZIN-2-ONES

[75] Inventors: Rodney B. Hargreaves, Poynton; Bernard J. McLoughlin; Stuart D. Mills, both of Macclesfield, all of England

[73] Assignee: Imperial Chemical Industries, PLC, London, England

[21] Appl. No.: 660,102

[22] Filed: Oct. 12, 1984

Related U.S. Application Data

[62] Division of Ser. No. 438,728, Nov. 3, 1982, Pat. No. 4,489,073.

[30] Foreign Application Priority Data

Nov. 12, 1981 [GB] United Kingdom ............... 8134174

[51] Int. Cl.[4] ............... C07D 409/04; A61K 31/54; C07D 409/06; C07D 417/04
[52] U.S. Cl. ............... 514/222; 544/8; 544/182; 544/68
[58] Field of Search ............... 544/8; 424/246; 514/222

[56] References Cited

U.S. PATENT DOCUMENTS 4,423,045 12/1983 Brown et al. ............... 544/8

Primary Examiner—John M. Ford

Attorney, Agent, or Firm—Cushman, Darby & Cushman

[57] ABSTRACT

Heterocyclic compounds of the formula:

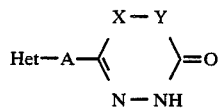

wherein A is a direct link, or is alkylene of 1 to 4 carbon atoms or alkenylene of 2 to 4 carbon atoms; wherein either X is $-CR^1R^2-$ and Y is $-O-$, $-S-$ or $-NR^3-$, wherein $R^1$, $R^2$ and $R^3$, which may be the same or different, each is hydrogen or alkyl of up to 4 carbon atoms;
or X is $-O-$, $-S-$ or $-NH-$ and Y is $-CR^1R^2-$ wherein $R^1$ and $R^2$ have the meanings stated above; and wherein Het is a 5- or 6- membered heterocyclic ring containing 1, 2 or 3 heteroatoms selected from nitrogen, oxygen or sulphur atoms, which ring may be unsubstituted or may bear one or two substituents as set out in claim 1, provided that when X is $-CR^1R^2-$ and A is a direct link, Het is not unsubstituted 2-furyl; and salts thereof where appropriate; processes for their manufacture and pharmaceutical compositions containing them. The compounds possess cardiotonic and/or antihypertensive activity.

19 Claims, No Drawings

1,3,4-THIADIAZIN-2-ONES

This is a division of application Ser. No. 438,728, filed Nov. 3, 1982, now U.S. Pat. No. 4,489,073.

This invention relates to new heterocyclic compounds, some of which possess cardiotonic properties, some of which possess antihypertensive properties and some of which possess both said properties.

Many 6-aryl-dihydropyridazin-3-one derivatives are known which possess pharmaceutical properties affecting the cardiovascular system. These are described in the journal of Medicinal Chemistry, 1974, 17, 273–286 and in the Journal of Heterocyclic Chemistry, 1974, 11, 755–761, and there is much related patent literature.

When an additional hetero-atom is inserted into the pyridazine nucleus, most of the simple structures have been described in the academic chemical literature. Thus, for example:

2-phenyl-4H,6H-1,3,4-thiadiazin-5-one and its 6-methyl analogue are known from Chemical Abstracts, 1948, 42, 5919 and 1956, 50, 7817;

5-phenyl-3H,6H-1,3,4-thiadiazin-2-one and its 6-methyl analogue are known from Leibig's Annalen der Chemie, 1977, 791 and from this article are also known the corresponding p-bromophenyl and 4-biphenylyl analogues;

2-phenyl-4H,6H-1,3,4-oxadiazin-5-one is known from Receuil des Travaux chimiques des Pays Bas, 1929, 48, 417 and o-hydroxyphenyl analogues thereof are known from J. Heterocyclic Chemistry, 1970, 7; 927;

3-phenyl-4,5-dihydro-5-methyl-1H-1,2,4-triazin-6-one is known from J. Heterocyclic Chemistry, 1978, 15, 1271;

6-phenyl-4,5-dihydro-2H-1,2,4-triazin-3-one and its 4-methyl analogue are known from Chemical Abstracts, 1970, 73, 35334.

From the patent literature 5-phenyl-3H,6H-1,3,4-oxadiazin-2-one and the corresponding 4-bromophenyl and 2-naphthyl analogues are known as blowing agents in the plastics industry, from U.S. Pat. Nos. 4,097,425, 4,105,848 and 4,158,094.

The only disclosure of thiadiazinone, oxadiazinone or triazinone derivatives which bear a heterocyclic substituent occurs in Receuil des Travaux chimiques des Pays Bas, 1964, 83, 1047 wherein there are described 5-(2-furyl)-3H,6H-1,3,4-thiadiazin- and oxadiazin-2-one, and 6-(2-furyl)-4,5-dihydro-2H-1,2,4-triazin-3-one. These compounds are said to have been prepared so that their bacteriostatic activity could be evaluated, but no details of this activity are given.

None of the abovementioned references discloses any pharmacological utility for any of the compounds described. The only references to pharmacological activity in this kind of compound of which applicants are aware appear in U.S. Pat. No. 3,514,455, which describes various 4,6-disubstituted-2-phenyl-4H,6H-1,3,4-thiadiazin-5-one derivatives which are claimed to possess antipyretic, analgesic, anti-inflammatory and antiedema activities, and in U.S. Pat. No. 3,946,010, which described various 3-o-aminophenyl-4,5-dihydro-1H-1,2,4-triazine-6-one derivatives which are claimed to possess anti-inflammatory activity.

A compound of considerable interest at present as a cardiotonic agent is a pyridone derivative known by the name AMRINONE, which has the structure:

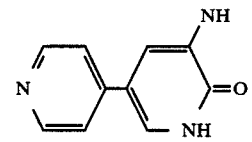

We have now found that various thiadiazinone, oxadiadinone or triazinone derivatives which are linked, directly or through a hydrocarbon chain, to a heterocyclic nucleus possess valuable cardiotonic and/or antihypertensive properties.

According to the invention there is provided a heterocyclic compound of the formula:

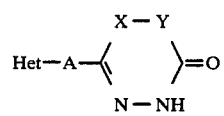

wherein A is a direct link, or is alkylene of 1 to 4 carbon atoms or alkylene of 2 to 4 carbon atoms;

wherein either X is —$CR^1R^2$ and Y is —O—, —S— or —$NR^3$—, wherein $R^1$, $R^2$ and $R^3$, which may be the same or different, each is hydrogen or alkyl of up to 4 carbon atoms;

or X is —O—, —S— or —NH— and Y is —$CR^1R^2$—, wherein $R^1$ and $R^2$ have the meanings stated above;

and wherein Het is a 5- or 6-membered heterocyclic ring containing 1, 2 or 3 heteroatoms selected from nitrogen, oxygen or sulphur atoms, which ring may be unsubstituted or may bear one or two substituents selected from:

halogen, cyano, nitro, trifluoro;

amino, alkylamino and dialkylamino wherein the one or two alkyls each is of up to 4 carbon atoms;

alkyl and alkoxy each of up to 4 carbon atoms;

hydroxy, oxo (if on carbon next to nitrogen) and oxy (if on nitrogen or sulphur);

substituents of the formula

—$CZOR^6$

—$CZNR^7R^8$

—$SO_2R^7R^8$ wherein Z is oxygen or sulphur and wherein $R^6$, $R^7$ and $R^8$, which may be the same or different, each is hydrogen, alkyl, alkenyl, cycloalkyl or alkoxyalkyl each of up to 6 carbon atoms, or aryl or arylalkyl each of up to 12 carbon atoms, or wherein $R^7$ and $R^8$ together with the adjacent nitrogen atom form a 5- or 6-membered fully-saturated heterocyclic ring;

and the substituent —CH=CH—CH=CH— (that is the substituent which forms a benzo-fused heterocyclic ring);

provided that when X is —$CR^1R^2$— and A is a direct link, Het is not unsubstituted 2-furyl;

or a salt thereof where appropriate.

A suitable value for A when it is alkylene is, for example, methylene or ethylene.

A suitable value for A when it is alkenylene is, for example, vinylene (—CH=CH—).

A suitable value for $R^1$, $R^2$ or $R^3$ when it is alkyl is, for example, methyl or ethyl.

A suitable halogen substituent in the heterocyclic ring Het is, for example, fluoro, chloro or bromo.

A suitable alkylamino or dialkylamino substituent in the heterocyclic ring Het is, for example, ethylamino or dimethylamino.

A suitable alkyl or alkoxy substituent in the heterocyclic ring Het is, for example methyl, ethyl, methoxy or ethoxy.

A suitable value for $R^6$, $R^7$ or $R^8$ when it is alkyl, alkenyl, cycloalkyl or alkoxyalkyl is, for example, methyl, ethyl, n-propyl, isopropyl, isobutyl, n-hexyl, allyl, cyclopentyl, cyclohexyl or methoxymethyl.

A suitable value for $R^6$, $R^7$ or $R^8$ when it is aryl or aralkyl is, for example, phenyl, tolyl, chlorophenyl, trichlorophenyl, benzyl or phenylethyl.

A suitable value for the heterocyclic ring formed by $R^7$, $R^8$ and the adjacent nitrogen atom is, for example, the pyrrolidino, piperidino or morpholino ring.

Specific values for Het are, for example, pyridyl, thienyl, furyl, pyrrolyl, pyrimidinyl, thiazolyl, imidazolyl, indolyl, benzothienyl, benzofuryl, quinolyl, isoquinolyl or quinoxalinyl, for example 2-, 3- or 4-pyridyl, 1-oxy-4-pyridyl, 2-thienyl, 3-thienyl, 2-furyl, 3-furyl, 2-pyrrolyl, 2-pyrimidinyl, 4-thiazolyl, 4-imidazolyl, 3-indolyl, 3-benzothienyl, 2-benzo[b]thienyl, 2-benzo[b]furyl, 3-benzo[b]furyl, 2-, 3- or 4-quinolyl, 1-isoquinolyl or 2-quinoxalinyl, any of which may bear one or two chloro, bromo, cyano, carbamoyl, nitro or methyl substituents.

An appropriate salt is an acid-addition salt, for example a hydrochloride, hydrobromide, acetate, oxalate, tartrate or citrate, of a compound wherein the group Het- is sufficiently basic to form an acid-addition salt; or a base-addition salt, for example a sodium, potassium, ammonium or benzylamine salt, of an acidic compound wherein $R^6$ is hydroxy.

A preferred heterocyclic compound of the invention has the formula stated above
wherein A is a direct link or is methylene or vinylene;
wherein either X is —$CH_2$— or —$CH(CH_3)$— and Y is —S—;
or X is —$CH_2$— and Y is —O— or —NH—;
or X is —S— and Y is —$CH_2$—, —$CH(CH_3)$—;

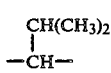

or —$C(CH_3)_2$—
or X is —O— or —NH— and Y is —$CH_2$—;
and wherein Het is 2-, 3- or 4-pyridyl which is unsubstituted or bears one chloro, bromo, cyano, carbamoyl or methyl substituent;
or Het is 2- or 3-thienyl which is unsubstituted or which bears one or two chloro or methyl substituents;
or Het is unsubstituted benzo[b]thienyl, benzo[b]furyl, indolyl or quinolyl;
or Het is 3-methyl-2-quinoxalinyl.

A particularly preferred heterocyclic compound which possesses cardiotonic activity has the formula stated above wherein A is a direct link, one of X and Y is —S— or —NH— and the other of X and Y is —$CH_2$— and Het is 2-, 3- or 4-pyridyl which is unsubstituted or which bears one chloro, bromo, cyano, carbamoyl or methyl substituent, or Het is unsubstituted 2-quinolyl or 3-indolyl.

A particularly preferred heterocyclic compound which possesses antihypertensive activity has the formula stated above wherein A is a direct link, X is —$CH_2$—, Y is —O—, —S— or —NH— and Het is 2-benzo[b]furyl, 3-benzo[b]thienyl, 2,5-dichlorothien-3-yl or 5-bromo- or 5-chloro-3-pyridyl.

Specific heterocyclic compounds of the invention are, for example:

5-(3-pyridyl-, 4-pyridyl-, 5-chloro-3-pyridyl-, 2-cyano-4-pyridyl-, 5-carbamoyl-2-pyridyl-, 6-carbamoyl-3-pyridyl-, 2-carbamoyl-4-pyridyl-, 2-benzo[b]furyl-, and 3-indolyl)-3H,6H-1,3,4-thiadiazin-2-one;

2-(2-pyridyl-, 3-pyridyl-, 4-pyridyl-, 6-methyl-2-pyridyl-, 5-bromo-3-pyridyl- and 2-quinolyl)-4H,6H-1,3,4-thiadiazin-5-one;

6,6-dimethyl-2-(4-pyridyl)-4H,6H-1,3,4-thiadiazin-5-one;

5-(2-benzo[b]furyl)-3H,6H-1,3,4-oxadiazin-2-one;

4-(4-pyridyl)-5,6-dihydro-1,2,4-triazin-6(1H)-one; and 6-(3-pyridyl-, 4-pyridyl-, 5-chloro-3-pyridyl-, 5-bromo-3-pyridyl-, 2,5-dichlorothien-3-yl- and 3-benzo[b]thienyl)-4,5-dihydro-1,2,4-triazin-3(2H)-one.

A preferred process for the manufacture of a compound of the invention wherein X is oxygen or sulphur and Y is —$CR^1R^2$— comprises the reaction of a hydrazide or thiohydrazide of the formula:

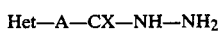

wherein Het and A have the meanings stated above and X is sulphur or oxygen, with an acid of the formula:

wherein $R^1$ and $R^2$ have the meanings stated above and wherein Hal is a halogen atom, for example the chlorine or bromine atom, or with a reactive derivative thereof.

When X is sulphur the acid is preferably used directly, or as a lower alkyl ester, for example the ethyl ester, thereof, and the reaction may be carried out in aqueous solution, in the presence of a base, for example, sodium hydroxide, at laboratory temperature.

When X is oxygen the acid is preferably used as a reactive derivative thereof, for example the acyl halide, and the reaction carried out in two stages. The acyl hydrazine may be reacted with the acyl halide in an inert solvent, for example dioxan or toluene, in the presence of a base, for example triethylamine or potassium carbonate. The diacyl hydrazine thus obtained may then be reacted with a base, for example sodium hydride, in a dipolar aprotic solvent, for example dimethylformamide, or with an alkali metal carbonate in dimethylformamide or acetone, and the reaction may be carried out at an elevated temperature, for example at between 60° and 100° C.

A preferred process for the manufacture of a compound of the invention wherein X is —$CR^1R^2$— and Y is sulphur comprises the reaction of a phenacyl halide of the formula:

wherein Het, A, $R^1$, $R^2$ and Hal have the meanings stated above, with a thiocarbazate of the formula:

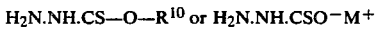

wherein $R^{10}$ is alkyl of up to 4 carbon atoms, for example methyl or ethyl, and wherein $M^+$ is an alkali metal or ammonium ion.

The reaction may be carried out in an organic diluent or solvent, for example acetonitrile or ethanol, at laboratory temperature or at an elevated temperature, for example at the boiling point of the diluent or solvent.

A preferred process for the manufacture of a compound of the invention wherein X is —$CR^1R^2$— and Y is oxygen comprises the cyclisation of a compound of the formula:

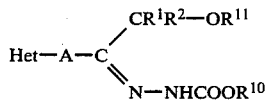

wherein Het, A, $R^1$, $R^2$ and $R^{10}$ have the meanings stated above and wherein $R^{11}$ is hydrogen or alkanoyl of up to 4 carbon atoms, for example acetyl. The cyclisation may be carried out in the presence of a base, for example sodium ethoxide, in a diluent or solvent, for example ethanol, at laboratory temperature.

The starting material for the last-mentioned reaction may be obtained by the reaction of a compound of the formula:

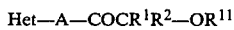

wherein Het, A, $R^1$, $R^2$ and $R^{11}$ have the meanings stated above, with an alkyl carbazate of the formula:

wherein $R^{10}$ has the meaning stated above.

A preferred process for the manufacture of a compound of the invention wherein X is —NH— and Y is —$CR^1R^2$— comprises the reaction of a compound of the formula:

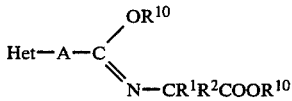

wherein Het, A, $R^1$, $R^2$ and $R^{10}$ have the meanings stated above (the two $R^{10}$ substituents being the same or different alkyl radicals of up to 4 carbon atoms), with hydrazine.

The reaction may be carried out in a diluent or solvent, for example ethanol, at a temperature up to the boiling point of the diluent or solvent.

The starting material for the last-mentioned reaction may be obtained either by the reaction of a compound of the formula:

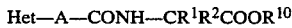

wherein Het, A, $R^1$, $R^2$ and $R^{10}$ have the meanings stated above, with an oxonium trifluoroborate of the formula $(R^{10})_3OBF_4$, wherein $R^{10}$ has the meaning stated above, or by the reaction of a compound of the formula:

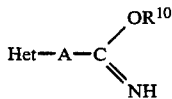

wherein Het, A and $R^{10}$ have the meanings stated above, with a glycine ester of the formula $H_2NCR^1R^2COOR^{10}$, wherein $R^1$, $R^2$ and $R^{10}$ have the meanings stated above.

A preferred process for the manufacture of a compound of the invention wherein X is —$CR^1R^2$— and Y is —$NR^3$— comprises the reaction of a compound of the formula:

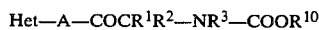

wherein Het, A, $R^1$, $R^2$, $R^3$ and $R^{10}$ have the meanings stated above, with hydrazine.

The reaction may be carried out in a diluent or solvent, for example ethanol, at a temperature up to the boiling point of the diluent or solvent.

The starting material for the last-mentioned process may be obtained by the reaction of a compound of the formula:

wherein Het, A, $R^1$, $R^2$ and $R^3$ have the meanings stated above, with a chloroformate of the formula $R^{10}OCOCl$, wherein $R^{10}$ has the meaning stated above.

A compound of the invention wherein $R^3$ is alkyl may be obtained by the alkylation of the corresponding compound wherein $R^3$ is hydrogen.

As stated above, some of the heterocyclic compounds of the invention possess cardiotonic activity. This may be demonstrated by their ability to increase the rate of change of aortic blood pressure in the anaesthetised cat. At a dose of the compound which produces an effective increase in said rate of change, that is, greater than a 25% increase, no symptom of toxicity is apparent.

As stated above, some of the heterocyclic compounds of the invention possess antihypertensive activity, as demonstrated by their ability to decrease the blood pressure of a normotensive cat or of a spontaneously hypertensive rat. The antihypertensive activity may also be demonstrated by the vasodilation effect produced by the heterocyclic compounds of the invention as shown by their ability to reduce spontaneous contraction in a rat portal vein preparation.

The heterocyclic compound of the invention may be administered to warm-blooded animals, including man, in the form of a pharmaceutical composition comprising as active ingredient at least one heterocyclic compound of the invention in association with a pharmaceutically-acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the heterocyclic compound of the invention, one or more drugs selected from sedatives, for example phenobarbitone, meprobamate, chlorpromazine and benzodiazepine sedative drugs, for example chlordiazepoxide and diazepam; vasodilators, for example hydralazine, glyceryl trinitrate, pentaerythritol tetranitrate and isosorbide dinitrate; diuretics, for example chlorothiazide, hydrochlorothiazide, amiloride, bendrofluazide or chlorthalidone; β-adrenergic blocking agents, for example propranolol or atenolol; cardiac membrane stabilising agents, for example quinidine; agents used in the treatment of Parkinson's disease and other tremors, for example benzhexol; and cardiotonic agents, for example digitalis preparations.

When used for the treatment of acute or chronic heart failure or of hypertension in man, it is expected that the heterocyclic compound would be given to man at a total oral dose of between 100 mg. and 2000 mg. daily, at doses spaced at 6–8 hourly intervals, or at an intravenous dose of between 5 mg. and 100 mg.

Preferred oral dosage forms are tablets or capsules containing between 50 and 500 mg., and preferably 100 mg. or 500 mg., of active ingredient. Preferred intravenous dosage forms are sterile aqueous solutions of the heterocyclic compound containing between 0.05% and 1% w/w of active ingredient, and more particularly containing 0.18% w/v of active ingredient.

The invention is illustrated but not limited by the following Examples:

EXAMPLE 1

A mixture of bromomethyl 4-pyridyl ketone hydrobromide (1.41 g.) ethanol (10 ml.) and a solution of ammonium thiocarbazate (1.64 g.) in water (5 ml.) was stirred at laboratory temperture for 15 hours and then evaporated to dryness under reduced pressure. The residue was stirred with water and the mixture was filtered. A mixture of the solid product, S-[2-oxo-2-(4-pyridyl)ethyl]thiocarbazate (1.0 g.), ethanol (15 ml.) and concentrated aqueous hydrochloric acid (0.2 ml.) was heated under reflux for 15 minutes, cooled and filtered. The solid product was crystallised from methanol and there was thus obtained 5-(4-pyridyl)-3H,6H-1,3,4-thiadiazin-2-one, m.p. 227°–228° C.

EXAMPLE 2

A mixture of bromomethyl 3-benzo[b]thienyl ketone (1.275 g.), methyl thiocarbazate (0.8 g.) and acetonitrile (80 ml.) was heated under reflux for 2 hours, kept at laboratory temperature for 24 hours and then filtered. The solid residue was crystallised from acetonitrile and there was thus obtained 5-(3-benzo[b]thienyl)-3H,6H-1,3,4-thiadiazin-2-one, m.p. 226°–228° C. (with decomposition).

The process described above was repeated using the appropriate bromomethyl ketone as starting material, and there were thus obtained the compounds described in the following table:

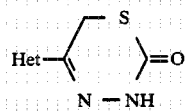

| Het | m.p. (°C.) | Crystallisation Solvent |
|---|---|---|
| 1-oxido-4-pyridyl | 228–230 (d) | methanol |
| 2-carbamoyl-4-pyridyl | 158–159 | (purified by chromatography) |
| 2-cyano-4-pyridyl | 199–203 | (purified by chromatography) |
| 3-pyridyl | 175–177 | ethanol |
| 5-bromo-3-pyridyl | 191–193 | ethanol |
| 5-chloro-3-pyridyl | quarter-hydrate 180–183 (d) | methanol |
| 6-carbamoyl-3-pyridyl | 308 | methanol |
| 4-carbmaoyl-2-pryidyl | 243–245 | ethanol |
| 5-nitro-2-pyridyl | 203–205 | toluene |
| 2-thienyl | 132–133 | methanol |
| 5-chloro-2-thienyl | 203–206 (d) | methanol |
| 2,5-dichloro-3-thienyl | 126–129 | ethyl acetate/petroleum ether (b.p. 60–80° C.) |
| 3-indolyl | 248–250 | methanol |
| 3-quinolyl | 239 (d) | ethanol |
| 3-methyl-2-quinoxalyl | 203–205 | (purified by chromatography |
| 2-benzo[b]furyl | 221–224 | ethyl acetate |
| 3-benzo[b]furyl | 178–181 | (purified by chromatography) |

The process described above was repeated using 1-bromoethyl 4-pyridyl ketone as starting material. There was thus obtained 6-methyl-5-(4-pyridyl)-3H,6H-1,3,4-thiadiazin-2-one, m.p. 172°–174° C. after crystallisation from methylene chloride.

EXAMPLE 3

Bromoacetic acid (7.0 g.) was added to a stirred mixture of pyridine-4-carbothiohydrazide (7.65 g.) and 2N-aqueous sodium hydroxide solution (25 ml.) and the mixture was stirred at laboratory temperature for 2 hours and then filtered. The filtrate was adjusted to pH 4 with concentrated aqueous hydrochloric acid, stirred at laboratory temperature for 15 minutes and then filtered. The solid product was crystallised from water (100 ml.) the solution being adjusted to pH 7 with saturated aqueous sodium bicarbonate solution, and there was thus obtained 2-(4-pyridyl)-4H,6H-1,3,4-thiadiazin-5-one, m.p. 193°–195° C.

The process described above was repeated using the appropriate carbothiohydrazide as starting material, and there were thus obtained the compounds described in the following table:

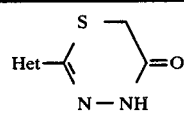

| Het | m.p. (°C.) | Crystallisation Sovent |
|---|---|---|
| 3-pyridyl | 183–187 | methanol |
| 5-bromo-3-pyridyl | 248–250° (d) | dimethylformamide |
| 2-pyridyl | 166–168 | ethyl acetate |
| 6-methyl-2-pyridyl | 167–169 | ethyl acetate |
| 2-thienyl | 128–130 | methanol |
| 3-thienyl | 139–141 | methanol |
| 3-benzo[b]thienyl | 188–191 | ethyl acetate/petroleum ether (b.p. 60–80° C.) |
| 2-quinolyl | 209–210 | methanol |
| 2-furyl | 124–126 | methanol |

The pyridine-4-carbothiohydrazide used as starting material was obtained as follows:

Pyridine (104.7 g.) was slowly added to a stirred mixture of pyridine-4-aldehyde (87.9 g.) and sulphur (39.5 g.), the exothermic reaction causing the mixture to boil, and after the addition was complete the mixture was stirred and heated under reflux for 90 minutes and then cooled. Water (500 ml.) was slowly added and the mixture was stirred for 1 hour and then filtered. The solid product was crystallised from cyclohexane and there was thus obtained N-(pyridine-4-carbothioyl)-piperidine, m.p. 115°–116° C.

A mixture of the above compound (10 g.), hydrazine hydrate (10 ml.) and methanol (30 ml.) was stirred at laboratory temperature for 2 hours, allowed to stand for 16 hours and then evaporated to dryness under reduced pressure. The residue was stirred with methanol, the mixture was filtered and the filtrate was evaporated to dryness under reduced pressure. There was thus obtained as an oil pyridine-4-carbothiohydrazide which was used without further purification.

The other carbothiohydrazides used as starting materials were similarly obtained from the appropriate heterocyclic aldehyde. Those carbothioylpiperidine intermediates which were characterised have the melting points shown in the following table:

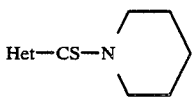

| Het | m.p. (°C.) |
| --- | --- |
| 3-pyridyl | 86–89* |
| 5-bromo-3-pyridyl | 110–112* |
| 6-methyl-2-pyridyl | 122–123 |
| 2-thienyl | 87–88 |
| 3-thienyl | 94–95 |
| 3-benzo[b]thienyl | 95–98 |
| 2-quinolyl | 128–130 |
| 2-furyl | 53–54 |

*Morpholine was used instead of piperidine, so the melting point is of the corresponding carbothioylmorpholine.

EXAMPLE 4

Ethyl 2-bromo-2-methylpropionate (3.7 ml.) was added to a stirred mixture of pyridine-4-carbothiohydrazide (3.82 g.) and 2N-aqueous sodium hydroxide solution (12.5 ml.), and sufficient methanol was then added to give complete solution. The mixture was stirred at laboratory temperature for 24 hours and evaporated to dryness under reduced pressure, and water was added to the residue. The mixture was filtered and the solid product was crystallised from isopropanol. There was thus obtained 6,6-dimethyl-2-(4-pyridyl)-4H,6H-1,3,4-thidiazin-5-one, m.p. 196°–197° C.

The process described above was repeated using either ethyl 2-bromopropionate or ethyl 2-bromo-3-methylbutyrate in place of ethyl 2-bromo-2-methylpropionate as starting material. There were thus obtained, respectively, 6-methyl-2-(4-pyridyl)-4H,6H-1,3,4-thiadiazin-5-one, m.p. 196°–198° C. after crystallisation from methanol, and 6-isopropyl-2-(4-pyridyl)-4H,6H-1,3,4-thiadiazin-5-one, m.p. 137°–138° C. after crystallisation from toluene.

EXAMPLE 5

Triethylamine (2.8 ml.) and chloroacetyl chloride (1.5 ml.) were successively added to a stirred solution of 2-(2-thienyl)acetohydrazide (3.12 g.) in dioxan (80 ml.) which was maintained at 10° C., and the mixture was stirred at laboratory temperature for 18 hours and then filtered. The solid residue was washed with ethyl acetate (100 ml.) and the combined filtrate and washings were evaporated to dryness under reduced pressure. The solid residue was crystallised from ethyl acetate and there was thus obtained $N^1$-chloroacetyl-$N^2$-2-(2-thienyl)acetylhydrazine, m.p. 152°–154° C.

Potassium carbonate (1.8 g.) was added to a stirred solution of the above diacylhydrazine (2.32 g.) in dimethylformamide (80 ml.) and the mixture was stirred at 60°–80° C. for 2 hours and then diluted with saturated aqueous sodium chloride solution (100 ml.) and extracted three times with ethyl acetate (80 ml. each time). The combined extracts were washed four times with water (100 ml. each time), dried over magnesium sulphate and evaporated to dryness under reduced pressure. The residue was purified by chromatography on a silica gel column (100 g.) using a 1:1 v/v mixture of ethyl acetate and petroleum ether (b.p. 60°–80° C.) as eluant. The product having an $R_F$ of 0.7 on silica gel plates using ethyl acetate as developing solvent was collected and crystallised from a mixture of ethyl acetate and petroleum ether (b.p. 60°–80° C.). There was thus obtained 2-(thien-2-ylmethyl)-4H,6H-1,3,4-oxadiazin-5-one, m.p. 94°–96° C.

EXAMPLE 6

A solution of sodium (0.45 g.) in ethanol (30 ml.) was added to a stirred solution of acetoxymethyl 2-benzo[b]furyl ketone ethoxycarbonylhydrazone (5.48 g.) in ethanol (30 ml.) and the mixture was stirred at laboratory temperature for 2 days. Further sodium (0.45 g.) in ethanol (30 ml.) was added and the mixture was stirred at laboratory temperature for a further 30 hours, diluted with water (300 ml.), adjusted to pH 5 with acetic acid and extracted with 100 ml. and then 50 ml. of ethyl acetate. The combined extracts were washed with saturated aqueous sodium chloride solution, dried and evaporated to dryness and the residue was purified by chromatography on a silica gel column (Merck 7734; 400 g.) using initially a 3:2 v/v mixture of petroleum ether (b.p. 60°–80° C.) and ethyl acetate as eluant. 7500 ml. of this eluant were used, the eluate being discarded, and elution was continued with ethyl acetate (1000 ml.). The eluate was evaporated to dryness under reduced pressure and the residue was stirred with a mixture of methanol and diethyl ether. The mixture was filtered and the solid residue was purified by chromatography on a silica gel column (Merck 9385; column size 25 cm. long and 20 mm. diameter) using a 1:1 v/v mixture of petroleum ether (b.p. 60°–80° C.) and ethyl acetate as eluant. The first 40 ml. of eluate were discarded and the next 90 ml. of eluate were evaporated to dryness under reduced pressure. The residue was stirred with a mixture of diethyl ether and petroleum ether (b.p. 60°–80° C.) and the mixture was filtered. There was thus obtained as solid product 5-(2-benzo[b]furyl)-3H,6H-1,3,4-oxadiazin-2-one, m.p. 209°–211° C.

The hydrazone used as starting material was obtained as folllows:

A mixture of 2-bromoacetylbenzo[b]furan (3.9 g.), sodium aetate (8.0 g.), concentrated aqueous hydrochloric acid (0.8 ml.), water (40 ml.) and ethanol (40 ml.) was heated under reflux for 75 minutes, cooled, concentrated to half-volume by evaporation under reduced pressure, and shaken with ethyl acetate (100 ml.) and water (50 ml.). The organic layer was retained, the aqueous layer was extracted with ethyl acetate (50 ml.) and the combined organic solutions were washed with saturated aqueous sodium chloride solution, dried and evaporated to dryness under reduced pressure.

A solution of the 2-acetoxyacetylbenzo[b]furan thus obtained (3.7 g.) and ethyl carbazate (1.94 g.) in ethanol (100 ml.) was heated under reflux for 21 hours and then evaporated to dryness under reduced pressure, and the residue was shaken with ethyl acetate (100 ml.) and saturated aqueous sodium chloride solution (50 ml.).

The organic layer was separated, washed with saturated aqueous sodium chloride solution, dried and evaporated to dryness under reduced pressure. There was thus obtained as residual oil acetoxymethyl 2-benzo[b]furyl ketone ethoxycarbonylhydrazone which was used without further purification.

EXAMPLE 7

A mixture of methyl N-(ethoxycarbonylmethyl)pyridine-4-carboximidate (9.0 g.), ethanol (100 ml.) and hydrazine hydrate (3.0 ml.) was kept at laboratory temperature for 15 hours and then filtered. The solid product was crystallised from methanol and there was thus obtained 4,5-dihydro-3-(4-pyridyl)-1,2,4-triazin-6(1H)-one, m.p. 269°–173° C.

The process described above was repeated using the appropriate imidate as starting material, and there were thus obtained the compounds described in the following table:

$$\text{Het—A}\diagdown\diagdown=O$$
with NH and N—NH

| Het | A | m.p. (°C.) | Crystallisation Solvent |
|---|---|---|---|
| 2-chloro-4-pyridyl | — | 280–283 (d) | ethanol |
| 2-thienyl | — | 248–250 | ethanol |
| 2-thienyl | —CH=CH— | 238–240 (d) | ethanol |
| 3-furyl | — | 183–185 | ethanol |

The methyl N-ethoxycarbonylmethylpyridine-4-carboximidate used as starting material was obtained as follows:

4-Cyanopyridine (5.2 g.) was added to a stirred solution of sodium (0.12 g.) in methanol (48 ml.) and the mixture was stirred at laboratory temperature for 22 hours, adjusted to pH 6 by dropwise addition of acetic acid and then evaporated to dryness. The residue was dissolved in ethyl acetate (100 ml.) and the solution was washed twice with saturated aqueous sodium chloride solution (50 ml. each time), dried over magnesium sulphate and evaporated to dryness under reduced pressure.

A mixture of methyl pyridine-4-carboximidate thus obtained (5.77 g.), glycine ethyl ester hydrochloride (29.59 g.), methylene chloride (120 ml.) and water (55 ml.) was vigorously stirred at laboratory temperature for 3 hours and the phases were then separated. The aqueous phase was extracted with methylene chloride (70 ml.) and the combined organic solutions were dried over magnesium sulphate and evaporated to dryness. There was thus obtained as residue methyl N-ethoxycarbonylmethylpyridine-4-carboximidate which was used without further purification.

The other imidates used as starting materials were similarly obtained from the corresponding cyanides.

EXAMPLE 8

A stirred mixture of methyl N-[2-(2,5-dichlorothien-3-yl)-2-oxoethyl]carbamate (2.68 g.), hydrazine hydrate (2 ml.) and ethanol (100 ml.) was heated under reflux for 2 hours, a solution of sodium (0.23 g.) in ethanol (20 ml.) was added and the mixture was stirred and heated under reflux for a further 16 hours and then evaporated to dryness under reduced pressure. The residue was shaken with water and ethyl acetate and the mixture was filtered. The solid product was crystallised from methanol and there was thus obtained 6-(2,5-dichlorothien-3-yl)-4,5-dihydro-1,2,4-triazin-3(2H)-one, m.p. 240°–242° C.

The process described above was repeated using the appropriate methyl or ethyl * carbamate as starting material, and there were thus obtained the compounds described in the following table:

$$\text{Het}\diagdown\diagdown=O$$
with NH and N—NH

| Het | m.p. (°C.) | Crystallisation Solvent |
|---|---|---|
| 4-pyridyl | 242–244 | aqueous methanol |
| 3-pyridyl | 198–200 | water |
| 5-chloro-3-pyridyl* | 184–187 | dimethylformamide |
| 5-bromo-3-pyridyl* | 287–289 (d) | dimethylformamide |
| 3-benzo[b]thienyl | 271–273 (d) | ethanol |
| 2,5-dimethyl-3-thienyl | 220–232 (d) | ethanol |

*ethyl carbamate used as starting material.

The methyl N-[2-(2,5-dichlorothien-3-yl)-2-oxoethyl]carbamate used as starting material was obtained as follows:

A solution of bromine (6.4 g.) in methylene chloride (30 ml.) was added to a stirred solution of 3-acetyl-2,5-dichlorothiophen (7.8 g.) in methylene chloride (100 ml.) and the mixture was stirred at laboratory temperature for 30 minutes, diluted with methylene chloride (50 ml.) and washed successively with water, saturated aqueous sodium bicarbonate solution and water, dried over magnesium sulphate and then added to a solution of hexamethylenetetramine (6.2 g.) in methylene chloride (100 ml.). The mixture was stirred at laboratory temperature for 16 hours and filtered, and the solid product was added to a stirred mixture of ethanol (100 ml.) and concentrated aqueous hydrochloric acid (20 ml.). The mixture was stirred at laboratory temperature for 16 hours, concentrated to 50 ml. by evaporation under reduced pressure, and filtered. The solid product, which consisted of 2-(2,5-dichlorothien-3-yl)-2-oxoethylamine hydrochloride, was washed with ethanol and then dissolved in water (100 ml.). A solution of methyl chloroformate (6.8 ml.) and benzyltriethylammonium chloride (0.1 g.) in ethyl acetate (100 ml.) was added, the mixture was stirred at laboratory temperature and sodium bicarbonate (14.8 g.) was added portionwise. The mixture was stirred at laboratory temperature for 16 hours and the phases were then separated. The aqueous phase was washed twice with ethyl acetate (100 ml. each time) and the combined ethyl acetate solutions were washed with water, dried over magnesium sulphate and evaporated to dryness under reduced pressure. The residue was crystallised from cyclohexane and there was thus obtained methyl N-[2-(2,5-dichlorothien-3-yl)-2-oxoethyl]carbamate, m.p. 96°–98° C.

The other carbamates used as starting materials were similarly prepared from the appropriate acetylheterocycle and methyl or ethyl chloroformate. Those carbamates which were characterised had melting points as follows:

Het—COCH$_2$NHCOOR$^{10}$

| Het | R[10] | m.p. (°C.) | Crystallisation Solvent |
|---|---|---|---|
| 4-pyridyl | methyl | 100–103 | diethyl ether |
| 3-pyridyl | methyl | hydrochloride 202–203 | diethyl ether/ ethanol |
| 5-chloro-3-pyridyl | ethyl | 118–124 | ethyl acetate |
| 5-bromo-3-pyridyl | ethyl | 107–110 | toluene |
| 3-benzo[b]thienyl | methyl | 121–122 | ethyl acetate |

What we claim is:

1. A heterocyclic compound of the formula:

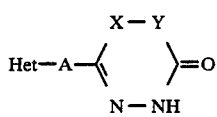

wherein A is a direct link, or is alkylene of 1 to 4 carbon atoms or alkenylene of 2 to 4 carbon atoms; wherein X is —CR$^1$R$^2$ and Y is —S— wherein R$^1$ and R$^2$, which may be the same of different, each is hydrogen or alkyl of up to 4 carbon atoms; and wherein Het is pyridyl, thienyl, furyl, pyrrolyl, pyrimidinyl, thiazolyl, imidazolyl, indolyl, benzothienyl, benzofuryl, quinolyl, isoquinolyl or quinoxalinyl which may be unsubstituted or may bear one or two substituents selected from: —halogen, cyano, nitro, trifluoromethyl; amino, alkylamino and dialkylamino wherein the one or two alkyls each is of up to 4 carbon atoms;

alkyl and alkoxy each of up to 4 carbon atoms;
hydroxy, oxo (if on carbon next to nitrogen) and oxy (if on nitrogen or sulphur);
substituents of the formula

—CZOR$^6$

—CZNR$^7$R$^8$

—SO$_2$R$^7$R$^8$ wherein Z is oxygen or sulphur and wherein R$^6$, R$^7$ and R$^8$, which may be the same or different, each is hydrogen, alkyl, alkenyl, cycloalkyl or alkoxyalkyl each of up to 6 carbon atoms, or aryl or arylalkyl each of up to 12 carbon atoms, or wherein R$^7$ and R$^8$ together with the adjacent nitrogen atom form a 5- or 6-membered fully-saturated heterocyclic ring;
provided that when A is a direct link, Het is not unsubstituted 2-furyl;
or a salt thereof where appropriate.

2. A heterocyclic compound as claimed in claim 1 wherein A is a direct link or is methylene or vinylene; wherein X is —CH$_2$— or —CH(CH$_3$)— and Y is —S—;
and wherein Het is 2-, 3- or 4-pyridyl which is unsubstituted or bears one chloro, bromo, cyano, carbamoyl or methyl substituent;
or Het is 2- or 3-thienyl which is unsubstituted or which bears one or two chloro or methyl substituents;
or Het is unsubstituted benzo[b]thienyl, benzo[b]furyl, indolyl or quinolyl;
or Het is 3-methyl-2-quinoxalinyl.

3. A heterocyclic compound as claimed in claim 1 wherein A is a direct link, Y is —S—, X is —CH$_2$— and Het is 2-, 3- and 4-pyridyl which is unsubstituted or which bears one chloro, bromo, cyano, carbamoyl or methyl substituent, or Het is unsubstituted 2-quinolyl or 3-indolyl.

4. A heterocyclic compound as claimed in claim 1 wherein A is a direct link, X is —CH$_2$—, Y is —S— and Het is 2-benzo[b]furyl, 3-benzo[b]thienyl, 2,5-dichlorothien-3-yl or 5-bromo- or 5-chloro-3-pyridyl.

5. A compound according to claim 1 which is 5-(3-pyridyl)-3H,6H-1,3,4-thiadiazin-2-one.

6. A compound according to claim 1 which is 4-pyridyl-3H,6H-1,3,4-thiadiazin-2-one.

7. A compound accordng to claim 1 which is 5-chloro-3-pyridyl-3H,6H-1,3,4-thiadiazin-2-one.

8. A compound according to claim which is 2-cyano-4-pyridyl-3H,6H-1,3,4-thiadiazin-2-one.

9. A compound according to claim 1 which is 5-carbamoyl-2-pyridyl-3H,6H-1,3,4-thiadiazin-2-one.

10. A compound according to claim 1 which is 6-carbamoyl-3-pyridyl-3H,6H-1,3,4-thiadiazin-2-one.

11. A compound according to claim 1 which is 2-carbamoyl-4-pyridyl-3H,6H-1,3,4-thiadiazin-2-one.

12. A compound according to claim 1 which is 2-benzo[b]furyl-3H,6H,-1,3,4-thiadiazin-2-one.

13. A compound according to claim 1 which is 3-indolyl-3H,,6H-1,3,4-thiadiazin-2-one.

14. A compound according to claim 1 which is 6-methyl-5-(4-pyridyl)-3H,6H-1,3,4-thiadiazin-2-one.

15. A pharmaceutical composition having cardiotonic activity, hypertensive activity or a combination thereof comprising as active ingredient at least one heterocyclic compound, claimed in claim 1, in association with a pharmaceutically-acceptable diluent or carrier therefore.

16. A composition as claimed in claim 15 which contains, in addition to the heterocyclic compound, one or more drugs selected from sedatives, vasodilators, diuretics, β-adrenergic blocking agents, cardiac membrane stabilising agents, agents used in the treatment of Parkinson's disease and other tremors, and cardiotonic agents.

17. A method for the treatment of acute or chronic heart failure in a warm-blooded animal in need of such treatment, which comprises administering to said animal an effective amount of a heterocyclic compound claimed in claim 1.

18. A method for the treatment of hypertension in a warm-blooded animal in need of such treatment, which comprises administering to said animal an effective amount of a compound as claimed in claim 1.

19. A process for the manufacture of a heterocyclic compound, claimed in claim 1, which comprises:

Het—A—COCR$^1$R$^2$—Hal wherein Het, A, R$^1$, R$^2$ and Hal have the meanings stated above, with a thiocarbazate of the formula:

H$_2$N.NH.CS—O—R$^{10}$ or H$_2$N.NH.CSO—M+ wherein R$^{10}$ is alkyl of up to 4 carbon atoms and wherein M+ is an alkali metal or ammonium ion.

* * * * *